United States Patent [19]

Roth

[11] Patent Number: 4,737,426

[45] Date of Patent: Apr. 12, 1988

[54] CYCLIC ACETALS OR KETALS OF BETA-KETO ESTERS OR AMIDES

[75] Inventor: Martin Roth, Giffers, Switzerland

[73] Assignee: Ciba-Geigy Corporation, Ardsley, N.Y.

[21] Appl. No.: 859,683

[22] Filed: May 5, 1986

[30] Foreign Application Priority Data

May 15, 1985 [CH] Switzerland ............... 2089/85

[51] Int. Cl.$^4$ .......... G03C 5/16; G03C 1/495
[52] U.S. Cl. ............... 430/17; 430/270; 430/192; 430/176; 430/311; 430/326; 430/189; 430/177; 430/179; 430/18; 549/370; 549/375; 549/448; 549/454
[58] Field of Search ........... 430/270, 192, 176, 311, 430/326, 189, 177, 179, 17, 18

[56] References Cited

U.S. PATENT DOCUMENTS

| | | | |
|---|---|---|---|
| 3,515,552 | 6/1970 | Smith | 430/281 X |
| 3,536,489 | 10/1970 | Smith | 430/253 |
| 3,779,778 | 12/1973 | Smith et al. | 430/270 |
| 3,954,475 | 5/1976 | Bonham et al. | 430/281 |
| 3,987,037 | 10/1976 | Bonham et al. | 430/281 X |
| 3,991,033 | 11/1976 | Sam | 430/270 X |
| 4,101,323 | 7/1978 | Buhr et al. | 430/270 X |
| 4,189,323 | 2/1980 | Buhr | 430/281 |
| 4,247,611 | 1/1981 | Sander et al. | 430/286 |
| 4,248,957 | 2/1981 | Sander et al. | 430/270 |
| 4,250,247 | 2/1981 | Sander et al. | 430/270 |
| 4,258,121 | 3/1981 | Kojima | 522/281 |
| 4,339,567 | 7/1982 | Green et al. | 522/11 |
| 4,356,252 | 10/1982 | Lee | 430/270 |
| 4,371,605 | 2/1983 | Renner | 430/281 |
| 4,383,025 | 5/1983 | Green et al. | 430/280 |
| 4,398,014 | 8/1983 | Green et al. | 522/31 |
| 4,411,823 | 10/1983 | Hageman et al. | 430/284 X |
| 4,505,858 | 3/1985 | Mayer | 540/1 |
| 4,506,006 | 3/1985 | Ruckert | 430/192 X |
| 4,510,290 | 4/1985 | Kirchmayr et al. | 522/33 |

FOREIGN PATENT DOCUMENTS 2120263 11/1983 United Kingdom .

Primary Examiner—Paul R. Michl
Assistant Examiner—Cynthia Hamilton
Attorney, Agent, or Firm—Luther A. R. Hall

[57] ABSTRACT

Compounds of formula I

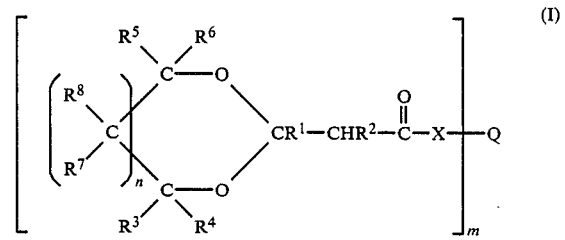

in conjunction with compounds that donate acid when exposed to actinic radiation, are suitable for use as positive photoresists. In formula I, $R^1$ and $R^2$ are hydrogen, alkyl, aryl, cycloalkyl, aralkyl or alkaryl, $R^3$ to $R^8$ are hydrogen or lower alkyl, X is —O— or —NR$^9$—, where $R^9$ is hydrogen or $C_1$–$C_4$alkyl, n is 0 or 1, m is 2, 3 or 4 and Q is an organic radical of valency m.

The photoresists are suitable for making printing forms, printed circuits, integrated circuits or silver-free photographic films.

11 Claims, No Drawings

CYCLIC ACETALS OR KETALS OF BETA-KETO ESTERS OR AMIDES

The present invention relates to cyclic acetals or ketals of β-keto esters or amides, to compositions containing these compounds in conjunction with compounds that release acid under conditions of photolysis, to a process for producing positive images using said compositions and to the use thereof for making printing plates, printed circuits, integrated circuits or silver-free photographic films.

Positive photoresist systems are known in the art. One type of these systems comprises a compound A that releases acid on exposure to radiation, a further compound B which undergoes reaction under the influence of an acid, and optionally a binder.

Images are produced by coating a substrate with the photoresist system and exposing the coated substrate to irradiation at selected areas. Compound A decomposes at the exposed areas and a protonic or Lewis acid forms. This acid in turn induces the chemical reaction of compound B. Compound B acts as solubility inhibitor for the binder, i.e. it is insoluble or only sparingly soluble in suitable solvents (developers). After its degradation, compound B loses this property and the exposed areas can be dissolved with a developer while the unexposed areas of the layer remain intact.

Positive photoresist systems that operate in accordance with this principle are described e.g. in German Offenlegungsschrift No. 2 718 254 or in U.S. Pat. No. 3,779,778. The solubility inhibitors used therein are special acetals or ketals.

Image-forming systems of the kind described above have a number of parameters that may influence the quality of the resulting image. Such parameters comprise e.g.: spectral sensitivity of the photoresist or quantum yield of the photopolymerisation (number of converted solubility inhibitors/amount of irradiation absorbed), adhesion of the unexposed layer on the substrate or differences in solubility between exposed and unexposed areas of the layer and the developer.

There is in particular a need to provide compounds that can be used in positive photoresists and which make is possible to obtain, on the one hand, very thin layers in the range from 0.5 to 10 μm and, on the other, very thick layers of up to 100 μm. In addition, there is a need for systems with which it is possible to ensure that the difference in solubility between the exposed areas and the unexposed areas are as great as possible.

Specifically, the present invention relates to compounds of formula I

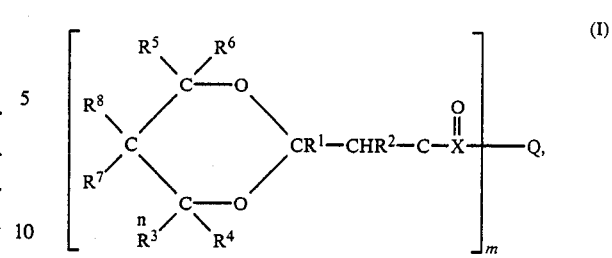

wherein $R^1$ and $R^2$ are each independently of the other hydrogen, $C_1$–$C_8$alkyl, phenyl, naphthyl, $C_5$–$C_7$cycloalkyl, $C_7$–$C_{14}$aralkyl or $C_7$–$C_{14}$alkaryl, which organic radicals may be substituted by one to three members selected from the group consisting of halogen, hydroxy, alkoxy, nitro, cyano and amino; $R^3$, $R^4$, $R^5$, $R^6$, $R^7$ and $R^8$ are each independently hydrogen or $C_1$–$C_4$alkyl, X is —O— or —$NR^9$—, where $R^9$ is hydrogen or $C_1$–$C_4$alkyl, n is 0 or 1, m is 2, 3 or 4, and Q is an aliphatic, cycloaliphatic, aromatic, araliphatic or 5- or 6-membered heterocyclic radical of valency m, with the proviso that where several ester or amide radicals are present in the molecule, the groups $R^1$ to $R^9$ within the scope of the above definitions may be different and, where n is 0, both carbon atoms are linked direct to each other to form a 5-membered heterocyclic radical.

$R^1$ and $R^2$ as $C_1$–$C_8$alkyl are straight chain or branched radicals. Examples of such radicals are methyl, ethyl, n-propyl, isopropyl, n-butyl, sec-butyl, n-pentyl, isoamyl, n-hexyl or n-octyl. Straight chain radicals are preferred, with methyl being particularly preferred. A further preferred meaning of $R^1$ is phenyl and hydrogen. $R^2$ is preferably hydrogen.

$R^3$ to $R^8$ as $C_1$–$C_4$alkyl may be methyl, ethyl, n-propyl, isopropyl or n-butyl, with methyl being preferred. $R^3$ to $R^8$ are preferably hydrogen.

$R^1$ and $R^2$ as $C_5$–$C_7$cycloalkyl may be cyclopentyl, cyclohexyl or cycloheptyl, with cyclohexyl being especially preferred.

$R^1$ and $R^2$ as $C_7$–$C_{14}$aralkyl may be benzyl, α-methylbenzyl, α, α-dimethylbenzyl or 2-phenylethyl, with benzyl being preferred.

$R^1$ and $R^2$ as $C_7$–$C_{14}$alkaryl may be o-, m- or p-tolyl, xylyl or mesityl, with tolyl being preferred.

$R^1$ and $R^2$ as organic radicals substituted by one to three members selected from the group consisting of halogen, alkoxy, nitro, cyano and amino, may be 2-hydroxyethyl, 2- or 3-hydroxypropyl, 2-, 3- or 4-hydroxyphenyl, 2-chloroethyl or 2-bromoethyl, 2-, 3- or 4-chlorophenyl, 2-, 3- or 4-chlorobenzyl, 2-, 3- or 4-nitrophenyl, 2-, 3- or 4-cyanophenyl, and 2-, 3- or 4-aminophenyl.

Q is a divalent, trivalent or tetravalent organic radical. Divalent radicals Q comprise e.g. straight or branched chain alkylene radicals which may be interrupted in the chain by hetero atoms such as —O— or —S—.

Straight or branched chain $C_2$–$C_{18}$alkylene radicals —$C_nH_{2n}$—(n=2–18) are preferred and straight chain $C_2$–$C_{12}$alkylene radicals are particularly preferred. Examples of groups of this type are: ethylene, trimethylene, tetramethylene, pentamethylene, hexamethylene, heptamethylene, octamethylene, nonamethylene, decamethylene, undecamethylene or dodecamethylene.

Eligible divalent radicals Q are also substituted or unsubstituted cycloalkylene groups. The alkyl moieties of alkyl-substituted cycloalkylene radicals may form part of the chain, for example in —CH$_2$—C$_6$H$_{10}$—CH$_2$—, or the substituents are in the position of a hydrogen atom, as in —(CH$_3$)C$_6$H$_8$(CH$_3$)—. Preferred radicals are those derived from cyclohexylene, i.e. 1,2-, 1,3- or 1,4-cyclohexylene, or also derivatives of bis(hydroxymethyl)cyclohexane after removal of both hydroxyl groups. The corresponding 1,4-cyclohexylene derivatives are particularly preferred.

Possible divalent radicals Q are also substituted or unsubstituted monocyclic arylene radicals. Examples of such radicals are o-, m- or p-phenylene or compounds that are derived from bis(hydroxymethyl)phenyl derivatives after removal of both hydroxyl groups. Preferred representatives of this last mentioned group are corresponding 1,3- or 1,4-derivatives.

Divalent aromatic radicals Q also encompass compounds containing several aromatic radicals, either condensed or also linearly fused. These compounds include in particular compounds of the formula

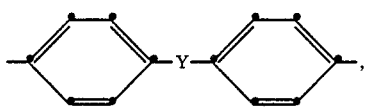

wherein Y is —CH$_2$—, —C(CH$_3$)$_2$, —O—, —S—, —SO$_2$— or —CO—.

Divalent heterocyclic radicals Q are derived e.g. from furan, pyran, thiophene or s-triazine.

A trivalent organic radical Q is e.g. a trivalent saturated aliphatic radical of the general formula C$_n$H$_{2n-1}$. Such radicals contain preferably from 3 to 9 carbon atoms. Attachment to the remainder of the molecule of formula I is through different carbon atoms. Preferred radicals are derived from glycerol or trimethylolpropane. Trivalent radicals may also, however, contain cycloaliphatic or aromatic groups. Preferred radicals of this type are derived from 1,3,5-trimethylolbenzene or from the corresponding hydrogenated cyclohexane derivative.

A tetravalent radical Q is e.g. a tetravalent aliphatic saturated radical of the general formula C$_n$H$_{2n-2}$. Such radicals contain preferably from 4 to 9 carbon atoms. A preferred representative of this group is derived from pentaerythritol. Attachment to the remainder of the molecule of formula I is through different carbon atoms. Tetravalent radicals Q may also, however, contain aromatic or cycloaliphatic groups. Preferred radicals of this type are derived from 1,2,4,5-tetramethylolbenzene or also from 3,3',4,4'-tetramethylolbenzophenone or the corresponding 1,1',2,2'-derivatives thereof. Tetravalent derivatives may also, however, be derived from the corresponding hydrogenated cycloaliphatic derivatives of the above mentioned aromatic tetramethylol compounds.

Preferred compounds of formula I are those wherein R$^1$ and R$^2$ are each independently of the other hydrogen, C$_1$-C$_4$alkyl or phenyl, R$^3$, R$^4$, R$^5$ and R$^6$ are each independently hydrogen or methyl, X is —O— or —NH—, n is 0, m is 2 or 3, and Q is an aliphatic, cycloaliphatic or araliphatic radical of valency m.

More preferred compounds of formula I are those wherein R$^1$ and R$^2$ are each independently of the other hydrogen, methyl or phenyl, R$^3$, R$^4$, R$^5$ and R$^6$ are hydrogen, X is —O— or —NH—, n is 0, m is 2, and Q is a divalent radical which is selected from the group consisting of C$_2$-C$_{18}$alkylene, xylylene or hexahydroxylylene.

Particularly preferred compounds of formula I are those wherein R$^1$ and R$^2$ are each independently of the other hydrogen, methyl or phenyl, R$^3$, R$^4$, R$^5$ and R$^6$ are hydrogen, X is —O— or —NH—, n is 0 and m is 3, and Q is derived from trimethylolpropane or glycerol after removal of the alcohol groups; and also those compounds of formula I wherein R$^1$ and R$^2$ are each independently of the other hydrogen, methyl or phenyl, R$^3$, R$^4$, R$^5$ and R$^6$ are hydrogen, X is —O— or —NH—, n is 0 and m is 4, and Q is derived from pentaerythritol after removal of the alcohol groups.

More especially preferred compounds of formula I are those wherein n is 0, as well as those wherein m is 2 or 3. Further preferred compounds are those wherein R$^1$ is methyl and R$^2$ to R$^8$ are hydrogen.

Most preferred are esters of formula I, i.e. compounds wherein X is —O—.

The β-acetal esters or amides of formula I are prepared by methods which are known per se.

In one process variant, a β-keto ester or amide of formula II is reacted with a diol of formula III to the corresponding acetal or ketal in accordance with the following reaction scheme 1:

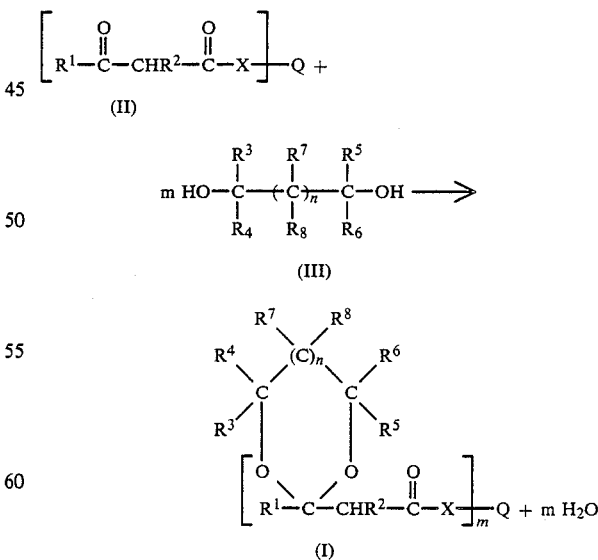

Herein the groups R$^1$ to R$^8$, X, Q and the indices m and n are as defined above.

The reaction is carried out in the presence of an acid catalyst. Examples of such catalysts are inorganic acids such as hydrochloric acid, sulfuric acid, nitric acid or phosphoric acid, or, also organic acids such as p-toluenesulfonic acid. The reaction can be carried out in the presence or absence of a solvent. Solvents are usually organic or inert. Examples of such solvents are: halogenated hydrocarbons such as methylene chloride, chloroform, carbon tetrachloride, dichloroethane or chlorobenzene; as well as aromatic solvents such as benzene, toluene or xylene. The choice of solvent for a specific reaction will depend on the respective reactants and can be determined by the skilled person by routine experimentation.

The $\beta$-keto esters or amides of formula II and the diols of formula III are compounds that are known per se. Some are commercially available or at least can be prepared by standard reactions of organic chemistry. For example, compounds of formula II can be prepared by reacting appropriate alcohols or amines with diketene. Another possibility of obtaining the compounds of formula I consists in transesterifying a $\beta$-acetal or $\beta$-ketal ester of formula IV with the polyhydric alcohol of formula V or in amidating the ester of formula IV with a polyvalent amine of formula V, as shown in the following reaction scheme 2:

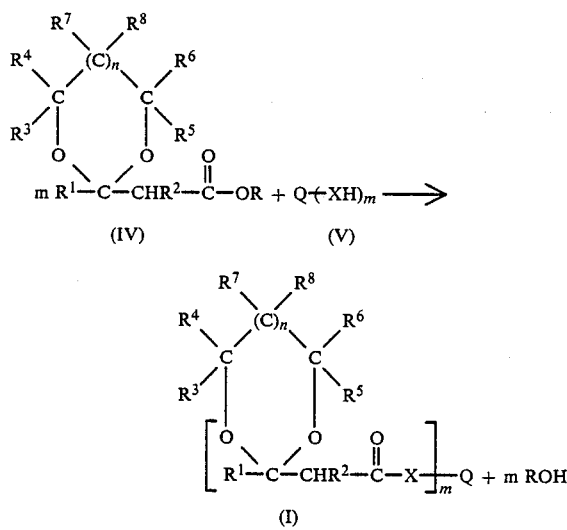

Herein the substituents $R^1$ to $R^8$, X, Q and the indices m and n are as defined above. R is a monovalent hydrocarbyl group, preferably $C_1$–$C_4$alkyl, most preferably methyl or ethyl.

the transesterification or amidation of scheme 2 is known per se and is normally carried out in the presence of a basic or acid catalyst, for example sodium hydroxide solution. Like the acetalation illustrated in scheme 1, the reaction may be carried out in the presence or absence of a solvent. The starting materials of formula V are per se known compounds and some are commercially available. The esters of formula IV can be prepared by the method outlined in scheme 1.

As already mentioned, the compounds of formula I can be used for the preparation of positive photoresist systems.

Accordingly, the invention also relates to compositions comprising (a) a compound of formula I as defined above, (b) a compound that releases acid when exposed to actinic radiation and (c) optionally a binder.

The amount of $\beta$-acetal or $\beta$-ketal of formula I is normally 5 to 50% by weight, based on the total amount of the composition. It is preferred to use 10 to 40% by weight of compound of formula I.

Photosensitive compounds that form or split off acid on exposure to light are known in large number. They include e.g. the diazonium salts used in producing diazotypes, the o-quinone diazides used in known positive copying compositions, or halogen compounds that form hydrohalic acids on exposure to radiation. Compounds of this type are disclosed e.g. in U.S. Pat. Nos. 3,515,552, 3,536,489 and 3,779,778, and in German Offenlegungsschrift specification Nos. 2 718 259, 2 243 621 and 2 610 842.

Suitable photosensitive components (b) of the compositions of this invention are also cationic photoinitiators selected from the group of the iodonium or sulfonium salts. Such compounds are described e.g. in "UV-Curing, Science and Technology" (Editor: S. P. Pappas, Technology Marketing Corp., 642 Westover Road, Stanford, Conn., U.S.A.) In particular, diaryliodosyl salts may also be used. Such compounds are disclosed e.g. in European patent application EP-A No. 106 797.

It is also possible to use sulfoxonium salts as photosensitive compounds. Such salts are disclosed e.g. in European patent specification No. 35 969 or in European patent application EP-A Nos. 44 274 and 54 509. Particularly suitable sulfoxonium salts are the aliphatic sulfoxonium salts disclosed e.g. in European patent application EP-A No. 164 314.

Particularly useful compounds are also those that form sulfonic acids on exposure to actinic light. Such compounds are known per se and are disclosed e.g. in UK patent application No. 2 120 263, European patent application EP-A Nos. 84 515, 37 152 and 58 638, and in U.S. Pat. Nos. 4,258,121 and 4,371,605.

Salts when employed as photosensitive acid donors (b) are preferably soluble in organic solvents. Most preferably, these salts are separation products with complex acids, for example of hydrofluoroboric acid or hexafluorophosphoric acid.

Depending on the nature and composition of the photosensitive mixture, the amount of photosensitive component (b) in the compositions of this invention can vary within wide limits. Good results are obtained with amounts of about 0.1 to 10% by weight of component (b), based on the total solids content. For thicker layers of more than 10 $\mu$m, it is advisable to use correspondingly less acid donor. It is preferred to use 0.2 to 5% by weight of acid donor, based on the total solids content of the radiation-sensitive composition.

A binder (c) may also be added to the positive photoresists of this invention. Such addition is particularly indicated whenever the photosensitive compositions are liquid or low viscosity mixtures. The amount of binder (c) can be from 30 to 90% by weight, preferably from 60 to 90% by weight, based on the total amount of compounds (a), (b) and (c).

the choice of binder is made in accordance with the utility and the necessary requirements therefor, e.g. the ability to develop in aqueous or aqueous/organic solvent systems or adhesion to substrates.

Examples of suitable binders (c) are novolaks that derive from an aldehyde, preferably acetaldehyde or furfuraldehyde, but preferably from formaldehyde, and a phenol. The phenolic component of these binders is preferably phenol itself or also a halogenated phenol, for example one substituted by one or two chlorine atoms, preferably p-chlorophenol, or it is a phenol that is substituted by one to two $C_1$–$C_9$alkyl groups, for example o-, m- or p-cresol, a xylenol, p-tert-butylphenol or p-nonylphenol. The phenol component of the preferred novalaks may also be p-phenylphenol, resorcinol, bis(4-hydroxyphenyl)methane or 2,2-bis(4-hydroxyphenyl)propane.

Some of the phenolic hydroxy groups of these novolaks can be modified by reaction with chloroacetic acid, isocyanates, epoxides or carboxylic acid anhydrides.

Futher suitable binders are e.g. copolymers of maleic anhydride with styrene or vinyl ethers or 1-alkenes, as well as copolymers of esters of acrylic acid or methacrylic acid with ethylenically unsaturated acids, for example methacrylic acid or acrylic acid.

It is preferred to use an alkali-soluble substance as binder, for example a novolak (unmodified or modified as described above), or copolymers of acrylates and methacrylates such as copolymers of methylmethacrylate/ethylacrylate/methacrylic acid.

Yet further auxiliary resins may be added to these alkali-soluble binders, as is customary in positive systems on a diazo-ketone basis. These auxiliary resins include e.g. vinyl polymers such as polyvinyl acetate, polyacrylates, poly(alkylmethacrylates) or poly(alkylacrylates), where alkyl contains 1 to 20 carbon atoms, polyvinyl ethers or polyvinylpyrrolidones. In general, however, not more than 20% by weight, based on the amount of alkali-soluble binder, of these resins will be added.

The compositions of this invention may contain further conventional modifiers such as stabilisers, pigments, dyes, fillers, adhesion promoters, levelling agents, wetting agents and plasticisers. For application, the compositions may also be dissolved in suitable solvents.

The compositions of this invention are pre-eminently suitable for use as coating agents for all kinds of substrates, e.g. wood, textiles, paper, ceramics, glass, plastics such as polyesters, polyethylene terephthalate, polyolefins or cellulose acetate, preferably in the form of films, as well as metals such as Al, Cu, Ni, Fe, Zn, Mg or Co, and Si and $SiO_2$, on which it is desired to produce an image by image-wise exposure. The coated substrates constitute a further object of the invention.

The invention further relates to a process for producing positive images comprising the following steps:

(a) coating a substrate with a photosensitive composition as defined above, (b) exposing the coated substrate to actinic radiation in a predetermined pattern, and (c) developing the exposed substrate.

The coated substrates can be prepared e.g. by treatment with a solution or suspension of the composition.

The choice of solvent and the concentration depends principally on the nature of the composition and on the coating method employed. The solution is applied uniformly to a substrate by known coating methods, e.g. by centrifuging, immersing, knife coating, curtain coating, brushing, spraying and reverse roller coating. It is also possible to apply the photosensitive layer to a temporary flexible support and then to coat the final substrate, e.g. a copper clad circuit board, by coat transfer by means of lamination.

The add-on (layer thickness) of photosensitive composition and nature of the substrate (layer support) depend on the desired field of application. A particular advantage of the compositions of this invention is that they can be used in widely varying layer thicknesses. This thickness range comprises values of about 0.5 μm to more than 100 μm. Layer thicknesses greater than 10 μm are no longer possible using conventional positive photoresist systems based on naphthoquinone diazide.

Possible utilities for the compositions of this invention are as photoresists in the electronics field (galvanoresist, discharge resist, solder stopping resist), the production of printing plates such as offset plates or silk screen printing formes, mould etching, or as microresist for making integrated circuits.

The possible substrates and the conditions for processing the coated substrates are correspondingly different. For example, sheets of polyester, cellulose acetate or plastics coated papers are used for photographic recording of information. Specially treated aluminium is used for offset formes and copper-clad laminates for making printed circuits. The layer thicknesses for photographic materials and offset formes are from about 0.5 to 10 μm and for printed circuits from 1 to about 100 μm.

After the substrate has been coated, the solvent is normally removed by drying to give a layer of photoresist on the substrate. After conventional image-wise exposure of the material, the exposed areas of the photoresist are washed out with a developer. The choice of developer depends on the nature of the photoresist, especially on that of the binder employed or of the resulting products of photolysis. The developer may consist of an aqueous soluton of base to which an organic solvent or a mixture of solvents may be added. It is preferred to use an aqueous solution of a base as developer. Acids cannot be used, as they would result in cleavage of the β-acetal or β-ketal ester (or of the corresponding amide) at the unexposed areas of the coated substrate, the consequence of which would be removal of the entire layer of photoresist.

Particularly suitable developers are the aquous alkaline solutions usef for the development of naphthoquinone diazide layers. These include in particular aqueous solutions of alkali metal silicates, phosphates and hydroxides. Small amounts of wetting agents and/or organic solvents may be added to these solutions.

Typical organic solvents that may be added to the developer solutions are e.g. cyclohexanone, 2-ethoxyethanol, toluene, acetone, and mixtures of two or more of these solvents. A typical aqueous/organic developer system is based on butylcellosolve/water (maximum water content: 30% by weight).

The term "exposure to actinic irradiation in a predetermined pattern" will be understood to mean exposure through a photomask containing a predetermined pattern, for example a photographic transparency, as well as exposure to a laser beam which is moved by logic control over the surface of the coated substrate to produce an image.

The photosensitivity of the compositions of the invention extends normally from the UV range (c. 200 nm) to c. 600 nm and is thus very wide ranging. Suitable light sources therefore comprise a large number of very widely varying types. Point light sources as well as arrays of reflector lamps are suitable. Examples are: carbon arcs, xenon arcs, mercury vapour lamps which may be doped with halogen atoms (metal halide lamps), fluorescent lamps, argon glow lamps, electronic flash lamps and photographic flood lamps. The distance between lamp and image material may vary substantially, depending on the utility and type of lamp, e.g. from 2 cm to 150 cm. Particularly suitable light sources are laser light sources, e.g. argon ion lasers or Kypton ion lasers with strong emission lines (Ar lasers) at 457, 476, 488, 514, 528 nm. With this type of exposure, a photomask in contact with the photopolymer layer is no longer necessary, as the laser beam writes direct onto the layer. The high sensitivity of the compositions of the invention is very advantageous here and permits high writing speeds at relatively low intensities. This method can be used to make printed circuits for the electronics industry, lithographic offset plates or relief printing plates as well as photographic image recording materials.

The photosensitive compositions may also contain sensitisers to increase the spectral sensitivity in a specific range of the electromagnetic spectrum. Such sensitisers include e.g. Michler's ketone, benzophenones, thioxanthones or aromatic hydrocarbons such as anthracene, pyrene or perylene.

Irradiation with electron beams is a further means of producing an image. Electron beams are able to decompose and also to crosslink the compositions of the invention thoroughly to give a negative image if the unexposed areas are removed by a solvent or by exposure without an original and development. At low intensity and/or at a higher writing speed, the electron beam effects a differentiation directed to higher solubility, i.e. the exposed areas of the layer can be removed by the developer. If the process is carried out with electron beams, suitable acid donors, in addition to the sensitive photolytic ones known for visible and close UV light, are also those whose absorption ranges lie in the shorter wavelength area of the electromagnetic spectrum and which are therefore less sensitive to daylight. This has the advantage that the recording materials can be handled without the exclusion of light and that the storage stability of the materials can be improved. Examples of such starters are tribromomethylphenylsulfone, 2,2',4,4',6,6'-hexabromodiphenylamine, pentabromoethane, 2,3,4,5-tetrachloroaniline, pentaerythritol tetrabromide, Clophenharz W, i.e. a chloroterphenyl resin, or chlorinated paraffins. The compositions of the invention have a very wide range of utilities. In particular, they are used where it is desired to produce a high resolution photolithographic image.

Accordingly, the invention also relates to the use of the compositions as defined above as positive photoresists for the production of printing plates, printed circuits or integrated circuits, as well as for silver-free photographic films. The invention further relates to the printing plates, printed circuits, integrated circuits or silver-free photographic films obtained with said compositions.

PREPARATORY EXAMPLES

Example 1

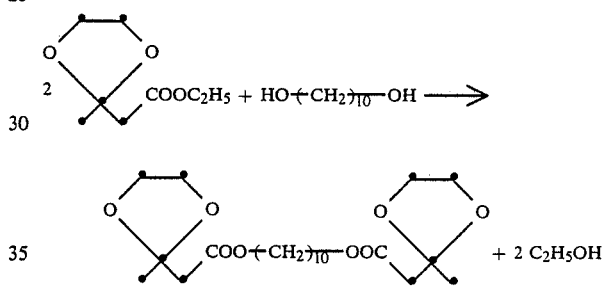

In a reactor equipped with stirrer, distillation head and nitrogen inlet, a mixture consisting of 522.6 g (3 moles) of ethyl acetoacetate ethylene acetal
174.3 g (1 mole) of 1,10-decanediol and
7.0 g of potassium cyanide is heated to 140° C. and the ethyl alcohol that forms is distilled off over 5 hours at this temperature under a weak flow of nitrogen. The cooled reaction mixture, which is diluted with 300 ml of toluene, is washed with a saturated aqueous solution of sodium carbonate and a saturated solution of sodium chloride and dried over potassium carbonate. The solvent is stripped off in a rotary evaporator and the residue is kept for 2 hours under a high vacuum at a bath temperature of 150° C., during which time excess ethyl acetoacetate acetal distills off (c. 150 g of distillate), to give 409 g (95% of theory) of the desired acetal diester as a brownish oil.

Elemental analysis: theory (%): C, 61.37; H, 8.90. found (%): C, 61.12; H, 8.96.

Thin-layer chromatography: Silica gel, eluant: methylene chloride/methanol=95/5 parts by volume; staining with potassium permanganate solution: 1 principal spot (product)+1 faint secondary spot $^1$H-NMR Spectrum (100 MHz; CDCl$_3$): δ values (ppm) 1.5 (s+m, 22H); 2.7 (S, 4H); 4.0 (s+m, 12H).

Example 2

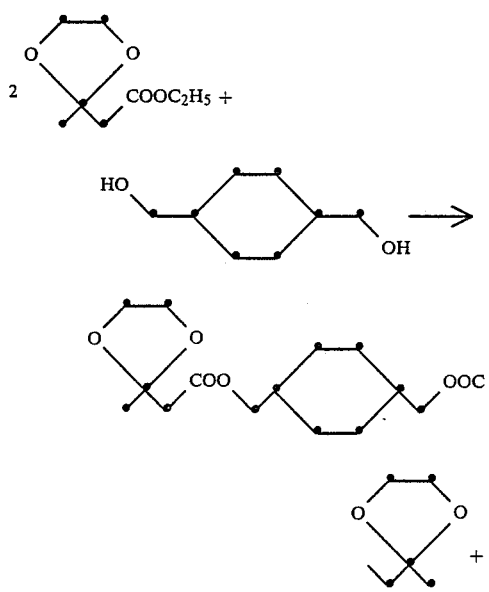

obtained by the procedure of Example 1 from:
20.9 g (0.12 mole) of ethyl acetoacetate ethylene acetal
7.2 g (0.04 mole) of 1,4-bis(hydroxymethyl)cyclohexane cis+trans (80% trans)
0.28 g of potassium cyanide.

Yield: 11.6 g (72% of theory) of the desired acetal diester as brownish oil.

Elemental analysis: theory (%): C, 59.93; H, 8.05. found (%): C, 60.15; H, 8.06.

Thin-layer chromatography: 1 principal spot+faint secondary spot $^1$H-NMR Spectrum (100 MHz; CDCl$_3$): δ values (ppm) 1.5 (s+m, 16H); 2.7 (s, 4H); 4.0 (s+m, 12H).

Example 3

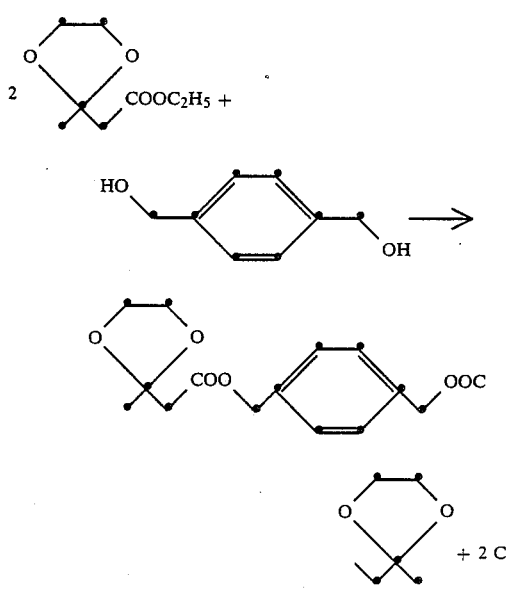

obtained by the procedure of Example 1 from:
10.45 g (0.06 mol) of ethyl acetoacetate ethylene acetal
2.76 g (0.02 mole) of 1,4-benzenedimethanol and
0.13 g of potassium cyanide.

Yield: 6.25 g (79% of theory) of the desired acetal diester as yellowish oil.

Elemental analysis: theory (%): C, 60.90; H, 6.64. found (%): C, 61.47; H, 6.68.

Thin-layer chromatography: 1 principal spot+faint secondary spot $^1$H-NMR Spectrum (100 MHz; CDCl$_3$): δ values (ppm) 1.5 (s, 6H); 2.7 (s, 4H); 4.0 (s, 8H); 5.1 (s, 4H): 7.3 (s, 4H).

Example 4

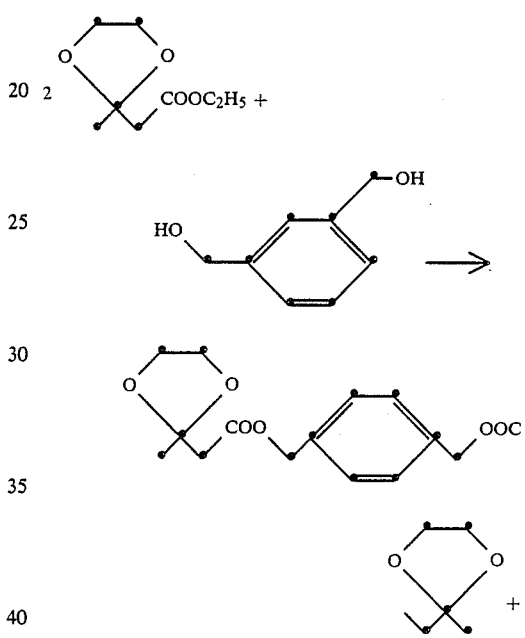

obtained by the procedure of Example 1 from:
10.45 g (0.06 mole) of ethyl acetoacetate ethylene acetal
2.76 g (0.02 mole) of 1,3-benzenedimethanol and
0.13 g of potassium cyanide.

Yield: 6.15 g of the desired acetal diester as yellowish oil.

Elemental analysis: theory (%): C, 60.90; H, 6.64. found (%): C, 61.27; H, 6.74.

Thin-layer chromatography Principal spot+faint secondary spot $^1$H-NMR Spectrum (100 MHz; CDCl$_3$): δ values (ppm) 1.5 (s, 6H); 2.7 (s, 4H); 4.0 (s, 8H); 5.1 (s, 4H); 7.3 (s, 4H).

Example 5

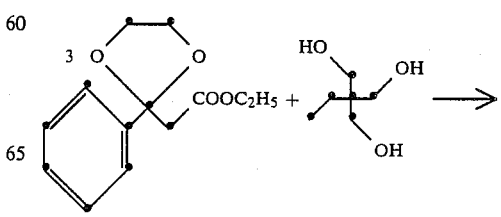

-continued

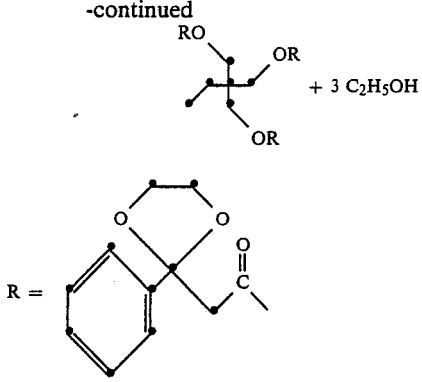

obtained by the procedure of Example 1 from:
18.90 g (0.08 mole) of ethyl benzoylacetate ethylene ketal
2.68 g (0.02 mole) of trimethylolpropane and
0.17 g of potassium cyanide.

Yield: 10.0 g (71% of theory) of the desired acetal triester as brownish resin.

Elemental analysis: theory (%): C, 66.47; H, 6.29. found (%): C, 67.01; H, 6.21.

$^1$H-NMR Spectrum (100 MHz; CDCl$_3$): δ values (ppm) 0.5–2.0 (m); 3.0 (s+m); 3.5–5.0 (m); 5.9 (s); 7.30 (m).

Example 6

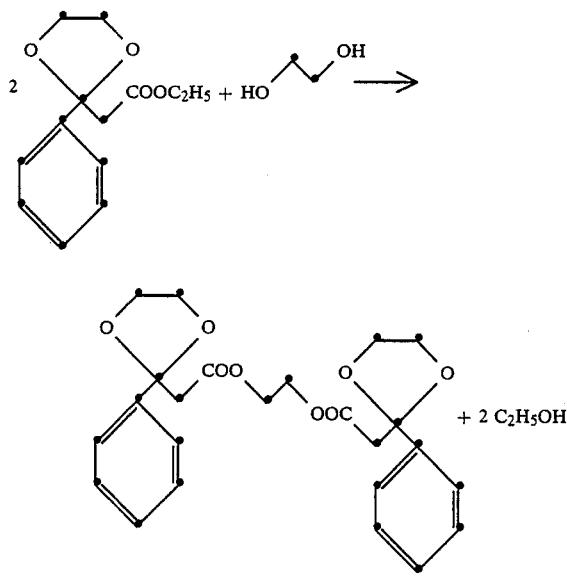

obtained by the procedure of Example 1 from:
27.35 g (0.12 mole) of ethyl benzoylacetate ethylene ketal
3.10 g (0.05 mole) of ethylene glycol and
0.74 g of a 30% solution of NaOCH$_3$ in CH$_3$OH.

Yield: 17.5 g (79% of theory) of the desired acetal diester as colourless oil.

Elemental analysis: theory (%): C, 65.15; H, 5.92. found (%): C, 65.32; H, 5.88.

1 principal spot+2 faint seconday spots $^1$H-NMR Spectrum (100 MHz; CDCl$_3$): δ values (ppm) 3.0 (m, 4H); 3.5–4.8 (m, 12H); 7.3 (m, 10H).

Example 7

(a)

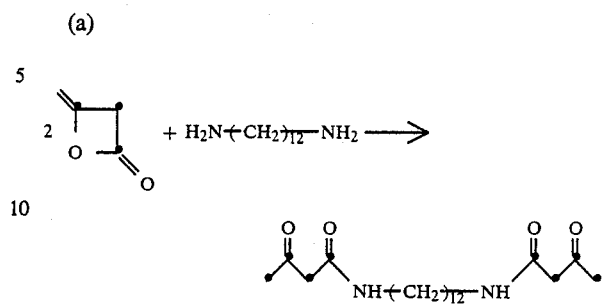

20.0 g (0.10 mole) of 1,12-diaminododecane in 150 ml of ethyl alcohol are cooled to 0° C. and 18.0 g (0.21 mole) of diketene are added dropwise over about 1 hour with cooling. The white suspension is diluted with 150 ml of ethyl alcohol and filtered. The residue is recrystallized hot from 250 ml of ethyl alcohol and dried (24 hours at 45° C. in vacuo), affording 30.0 g (81% of theory) of the bis(acetoacetamide) as colourless crystalline product with a melting point of 155°–156° C.

Elemental analysis: theory (%): C, 65.19; H, 9.85; H, 7.60; C, 65.25; H, 9.73; N, 7.57.

(b)

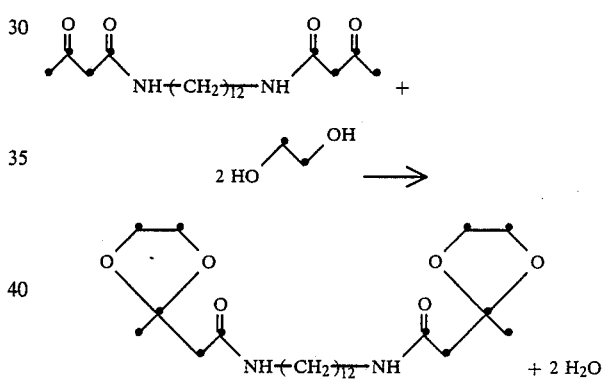

A mixture of
29.5 g (0.08 mole) of bis(acetoacetamide) obtained in (a)
11.9 g (0.19 mole) of ethylene glycol
0.16 g of p-toluenesulfonic acid
30 ml of chlorobenzene
15 ml of benzene
is refluxed for 8 hours in a water separator (after 4 hours a further 2 ml of ethylene glycol are added). The batch is cooled to room temperature and the suspension is filtered. The filter cake is dried (4 hours at 80° C. in vacuo), according 34.0 g (93% of theory) of the desired acetal diamide as a colourless crystalline product with a melting point of 92°–103° C.

Elemental analysis: theory (%): C, 63.13; H, 9.71; N, 6.14. found (%): C, 63.18; H, 9.71; N, 6.03.

Thin-layer chromatography: Silica gel, eluant: methylene chloride/methanol=95/5 parts by volume; staining with iodine: 1 principal spot (product).

$^1$H-NMR Spectrum (100 MHz; CDCl$_3$): (a) δ values (ppm) 1.1 (m); 2.1 (s); 2.8–3.5 (m). (b) δ values (ppm) 1.1 (m, 26H); 2.6 (s, 4H); 3.3 (m, 4H), 4.0 (s, 8H), 6.5 (s (broad), 2H).

USE EXAMPLES

Particulars of the developers employed
Developer A:
   75.0 g of sodium metasilicate pentahydrate
   0.4 g of Supronic® B50 [ABM Chemicals Ltd. Stockport, Cheshire SK61PQ/GB]; monionic wetting agent
   925 g of deionised water
Developer B: developer A+H$_2$O=4+1 (parts by vol.)
Developer C: developer A+H$_2$O=1+1 (parts by vol.)

Example I

Coating solution

| | |
|---|---|
| Alnovol ® PN 430 (novolak ex Hoechst), 25% solution in ethyl glycol acetate | 8.00 g |
| acetal diester of Example 1, 25% solution in ethyl glycol acetate | 2.00 g |
| [diphenyliodonium PF$_6$ structure] | 0.125 g |
| Orasol Red B dye (Ciba-Geigy) | 0.0125 g |

The solution is coated with an applicator in a c. 20 μm wet film to an anodised and electrolytically roughened aluminium sheet (offset plate substrate) and the film is dried for 15 minutes at 80° C. A dry coating of 4 g/m$^2$ is obtained.

Exposure is made through a test wedge as is customary in the offset plate copy (UGRA wedge, Switzerland). The light source is a 5000 watt metal halide lamp (Sylvania M 061) at a distance of 65 cm from the vacuum frame. The exposed coating is developed with developer C by gentle rubbing with cotton wool.

Result exposure time: 60 seconds
development time: 30 seconds with developer C at 20° C.
half-tone wedge steps:
  1-3 removed
  4-6 attacked The unexposed surface is not attacked even after 4 minutes in developer C.

Examples II-VI

Exposure tests are carried out through a test wedge as described in Example I, but using other acetal diesters.

Results:

| Example | II | III | IV | V | VI |
|---|---|---|---|---|---|
| acetal diester of Example | 2 | 3 | 4 | 5 | 7b |
| dry coating (g/m$^2$) | 4.3 | 5.5 | 4.6 | 6.9 | 6.0 |
| exposure time (sec.) | 60 | 60 | 60 | 60 | 60 |
| developer | B | B | B | A | C |
| developing time (sec.) | 30 | 15 | 15 | 300 | 240 |
| half-tone wedge, removed | 1-3 | 1-2 | 1-2 | 1 | 1 |
| half-tone wedge, attacked | 4-6 | 3-5 | 3-5 | 2-4 | 2-4 |

Example VII

This Example illustrates a coating on copper as used for making a printed circuit board.

Coating solution

A coating solution as prepared in Example I is used. A cleaned copper-clad printed circuit board is coated with this solution (20 μm wet film) with an applicator. The coating is then dried for 15 minutes at 80° C.

Exposure is made for 60 seconds through a Stauffer sensitivity guide in the apparatus described in Example I (increments of the optical density=0.15).

Result exposure time: 60 seconds
development time: 60 seconds in developer C at 20° C.
half-tone steps:
  1-4 removed
  5-7 attacked The developed resist image can be used as etching mask for etching away copper in the customary baths (e.g. FeCl$_3$ solution).

Example VIII

This Example illustrates the production and processing of a thick layer (50 μm) on copper.

Coating solution

| | |
|---|---|
| Alnovol ® PN 430, 50% solution in ethyl glycol acetate | 4.00 g |
| acetal diester of Example 1, 50% solution in ethyl glycol acetate | 1.00 g |
| [diphenyliodonium PF$_6$ structure] | 0.125 g |
| Orasol Red B dye (Ciba-Geigy) | 0.0125 g |

The solution is coated on a copper-clad printed cirucit board with an applicator (100 μm wet film) as in Example I. The coating is dried for 30 minutes at 100° C. The photosensitive layer has a thickness of c. 50 μm. Exposure is made using the light source described in Example I. The Stauffer test wedge (Example VII) is used as a pattern generator as well as a conductive pattern.

Result exposure time: 60 seconds
development time: 4 minutes with developer C at 20° C.
half-tone steps:
  1-5 removed
  6-7 attacked The developed resist image can be used e.g. as galvanoresist for semi-additive technology.

The short exposure time of 60 seconds for a layer thickness of 50 μm is remarkable.

Example IX

This Example is carried out by the same procedure as described in Example 1, except that 2-(4-methoxystyryl)-4,6-bistrichloromethyl-s-triazine (Example 1 of German Offenlegungsschrift No. 2 243 621) is used as acid donor instead of diphenyliodonium hexafluorophosphate. The light source is a 2000 watt metal halide at a distance of 75 cm.

Result acetal diester: according to Example 1
dry coating: 4.6 g/m²
exposure time: 60 seconds
developer: type A
development time: 180 seconds
half-tone wedge:
  1-3 removed
  4-5 attacked

What is claimed is:

1. A process for producing a positive image which comprises
   (a) coating a substrate with a photosensitive composition which comprises
      (i) a compound of formula I

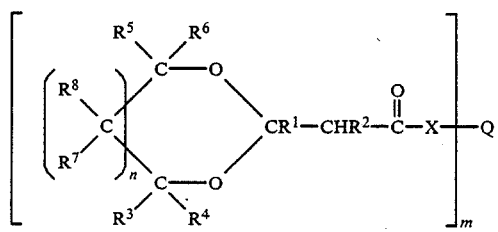

wherein $R^1$ and $R^2$ are each independently of the other hydrogen, $C_1$-$C_8$-alkyl, phenyl, naphthyl, $C_5$-$C_7$-cycloalkyl, $C_7$-$C_{14}$-aralkyl or $C_7$-$C_{14}$-alkaryl, or said alkyl, said phenyl, said napthyl, said cycloalkyl, said aralkyl or said alkaryl substituted by one to three members selected from the group consisting of halogen, hydroxy, alkoxy, nitro, cyano and amino, $R^3$, $R^4$, $R^5$, $R^6$, $R^7$ and $R^8$ are each independently hydrogen or $C_1$-$C_4$-alkyl, X is —O— or —$NR^9$— where $R^9$ is hydrogen or $C_1$-$C_4$-alkyl, n is 0 or 1, m is 2, 3 or 4, and Q is an aliphatic, cycloaliphatic, aromatic, araliphatic or 5- or 6-membered heterocyclic radical of valency m, with the proviso that where several ester or amide radicals are present in the molecule, the groups $R^1$ to $R^9$ within the scope of the above definitions are the same or different, and where n is 0, both carbon atoms are linked direct to each other to form a 5-membered dioxolane ring, (ii) an effective amount of a photosensitive compound which releases an acid upon exposure to actinic radiation, (b) exposing the coated substrate to actinic radiation in a predetermined pattern through a photomask, and (c) developing the positive image by removing the exposed areas with a developer.

2. A process according to claim 1 wherein the photosensitive composition of step (a) additionally contains (iii) a binder.

3. A process according to claim 1 where in the compound of formula I of step (a) $R^1$ and $R^2$ are each independently of the other hydrogen, $C_1$-$C_4$-alkyl or phenyl, $R^3$, $R^4$, $R^5$ and $R^6$ are each independently hydrogen or methyl, X is —O— or —NH—, n is 0, m is 2 or 3, and Q is an aliphatic, cycloaliphatic or araliphatic radical of valency m.

4. A process according to claim 1 where in the compound of formula I of step (a) $R^1$ and $R^2$ are independently of the other hydrogen, methyl or phenyl, $R^3$, $R^4$, $R^5$ and $R^6$ are hydrogen, X is —O— or —NH—, n is 0, m is 2, and Q is a divalent radical which is selected from the group consisting of $C_2$-$C_{18}$-alkylene, xylylene and hexahydroxylylene.

5. A process according to claim 1 where in the compound of formula I of step (a) $R^1$ and $R^2$ are each independently of the other hydrogen, methyl or phenyl, $R^3$, $R^4$, $R^5$ and $R^6$ are hydrogen, X is —O— or —NH—, n is 0, m is 3, and Q is derived from trimethylolpropane or glycerol after removal of the alcohol groups.

6. A process according to claim 1 where in the compound of formula I of step (a) $R^1$ and $R^2$ are each independently of the other hydrogen, methyl or phenyl, $R^3$, $R^4$, $R^5$ and $R^6$ are hydrogen, X is —O— or —NH—, n is 0, m is 4, and Q is derived from pentaerythritol after removal of the alcohol groups.

7. A process according to claim 1 where in the compound of formula I of step (a) n is 0.

8. A process according to claim 1 where in the compound of formula I of step (a) m is 2 or 3.

9. A process according to claim 1 where in the compound of formula I of step (a) $R^1$ is methyl and each of $R^2$ to $R^8$ is hydrogen.

10. A process according to claim 1 where in the compound of formula I of step (a) X is —O—.

11. A positive image prepared according to the process of claim 1.

* * * * *